United States Patent [19]
Thompson

[11] Patent Number: 6,089,231
[45] Date of Patent: Jul. 18, 2000

[54] CONTOURED MICRO-CONDOM WITH RADIALLY STRETCHING APPLICATOR

[76] Inventor: Harry Thompson, 787 N. Sunrise Way, Palm Springs, Calif. 92262

[21] Appl. No.: 08/785,252

[22] Filed: Jan. 17, 1997

Related U.S. Application Data

[63] Continuation of application No. 08/613,463, Mar. 11, 1996, abandoned.

[51] Int. Cl.$^7$ .................................................. A61F 6/02
[52] U.S. Cl. .......................... 128/842; 128/844; 128/918
[58] Field of Search .................................. 128/842, 844, 128/918; 604/347–353

[56] References Cited

U.S. PATENT DOCUMENTS

| | | | |
|---|---|---|---|
| D. 254,808 | 4/1980 | Meldahl | 128/844 |
| 2,548,149 | 4/1951 | Fowler | 604/352 |
| 3,037,508 | 6/1962 | Friedman | 604/349 |
| 4,320,752 | 3/1982 | Comparetto | 604/349 |
| 4,795,425 | 1/1989 | Pugh | 128/844 |
| 4,820,290 | 4/1989 | Yahr | 604/349 |
| 4,869,269 | 9/1989 | Sharkan | 128/844 |
| 5,479,940 | 1/1996 | Babled | 128/842 |
| 5,482,053 | 1/1996 | Kelly | 128/844 |
| 5,549,120 | 8/1996 | Persson | 128/844 |

*Primary Examiner*—Michael A. Brown
*Attorney, Agent, or Firm*—Marianne S. Hamilton, Esq.

[57] ABSTRACT

A contoured micro-condom has been designed together with a self-contained easy and carefree combination applicator and package. The micro-condom, which has a thin impervious sheath in the general shape of the glans penis head contours, has a thicker elastic band around its open end. The micro-condom's band is positioned securely and is contained within an apperature within the retainer frame of the applicator/package, the apperature having sufficient width to accommodate the diameter of a nominal erect glans penis head. In this position, the contoured or other micro-condom is covered at its closed end by a unidirectional releasing top cover, and is covered on its open end by another removable lower cover. Thus, it is protected from the outside environment, and ready to be applied using a few quick, easy and carefree steps. Quick removal of the lower cover allows access to the open end of the micro-condom which is placed over the erect glans penis head as it pushes through the unidirectional releasing top cover and releases its band from the frame of the applicator/package. The novel unidirectional releasing cover is specially constructed in material and/or geometry, to allow the cover to change shape and size easily with the application of pressure in one direction while resisting a shape or size change from the other direction. This allows the applicator to also act as a safe packaging for the micro condom.

20 Claims, 4 Drawing Sheets

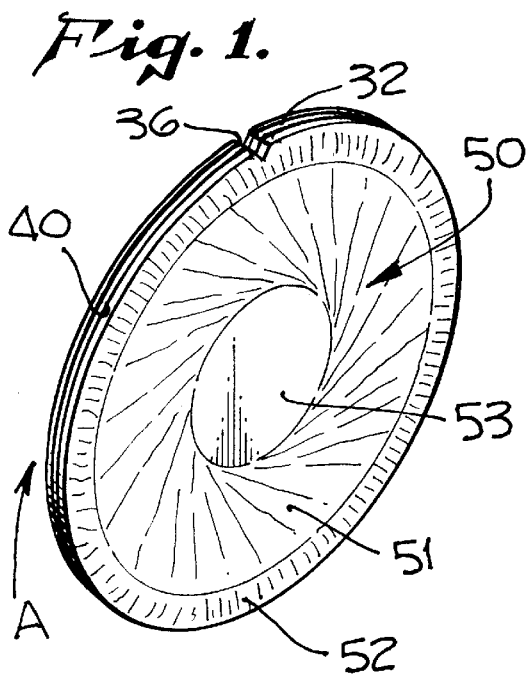
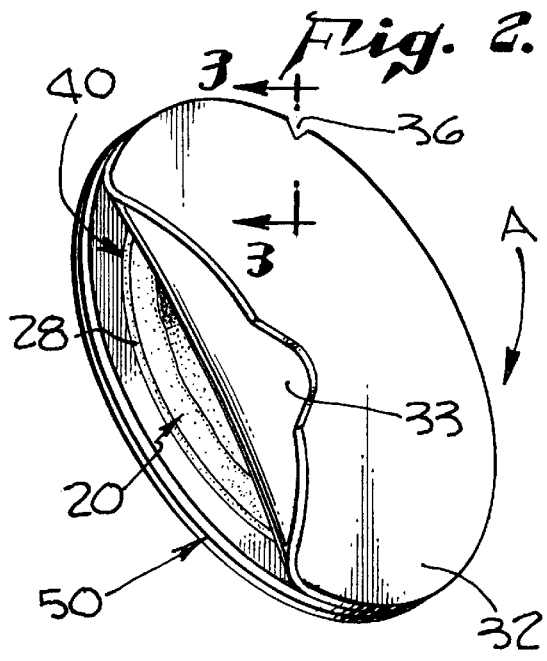
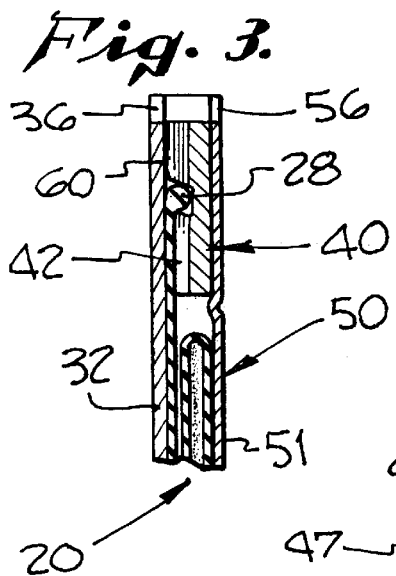
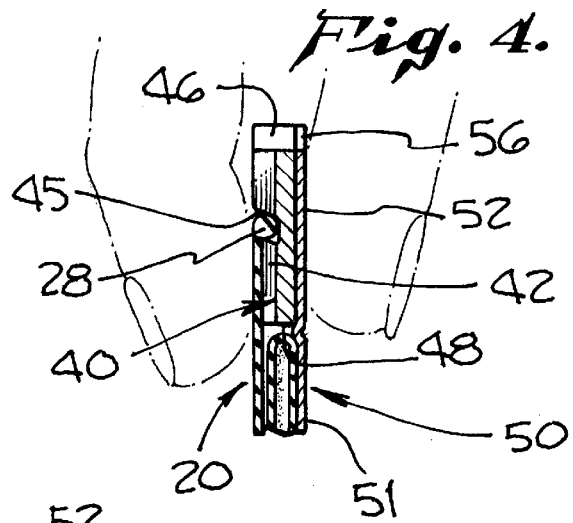
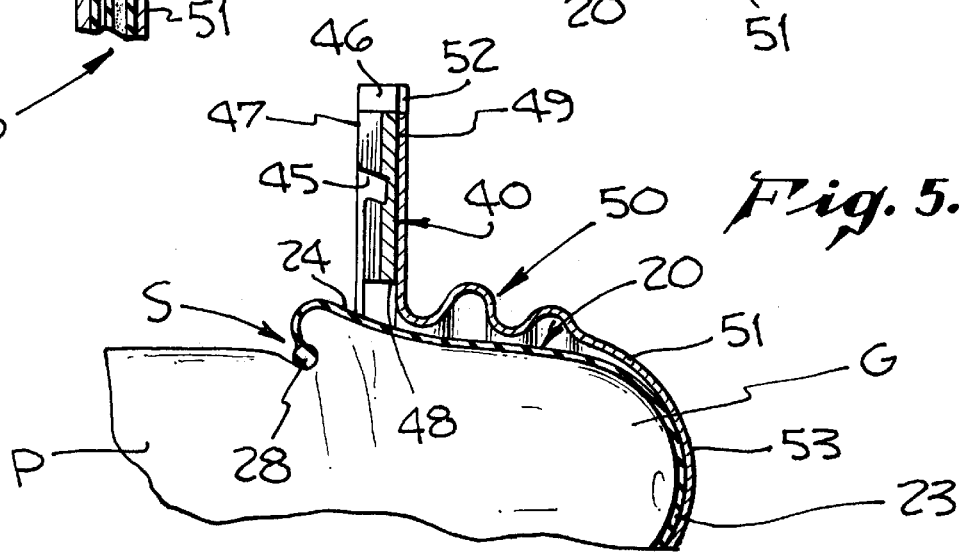

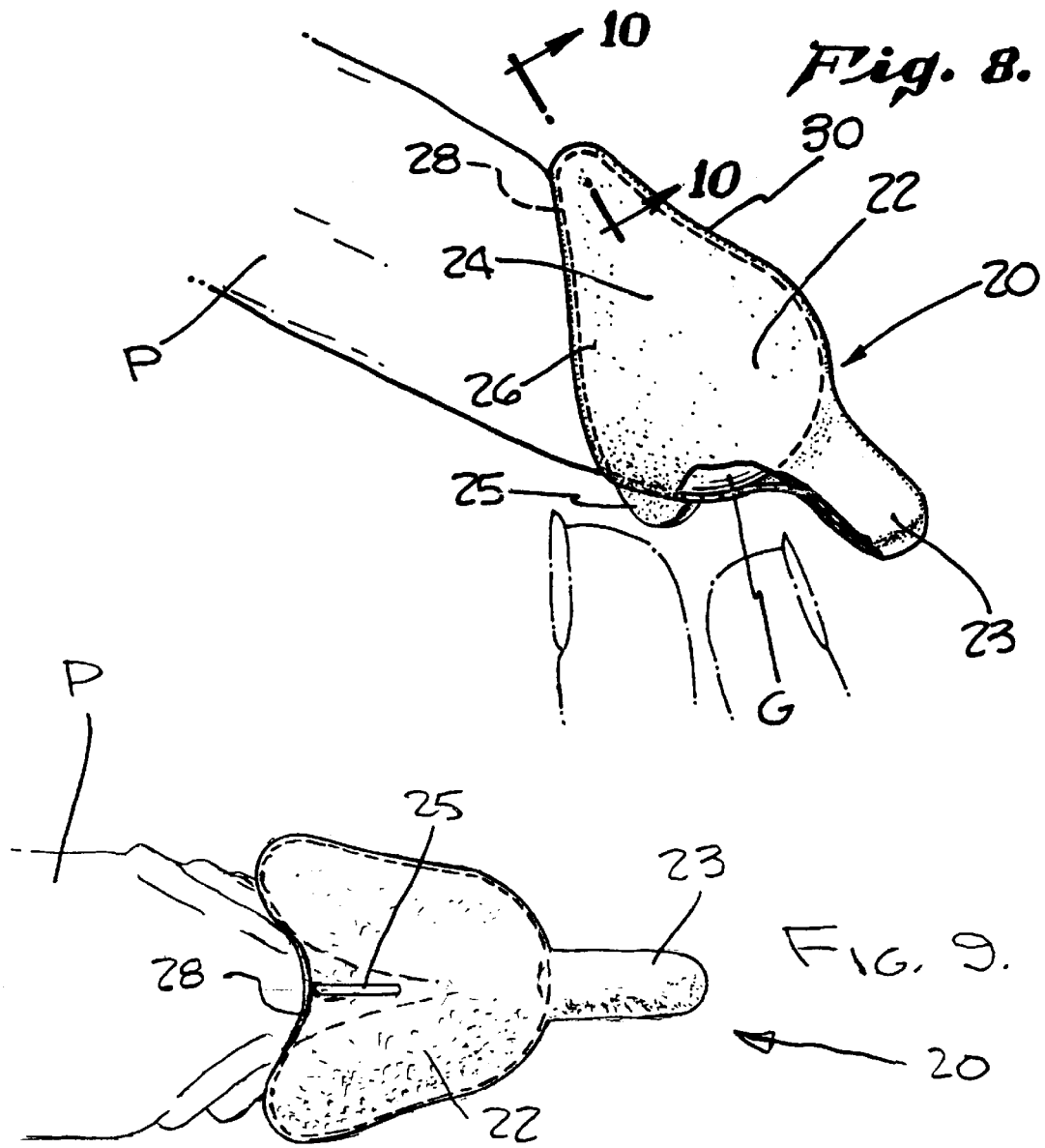
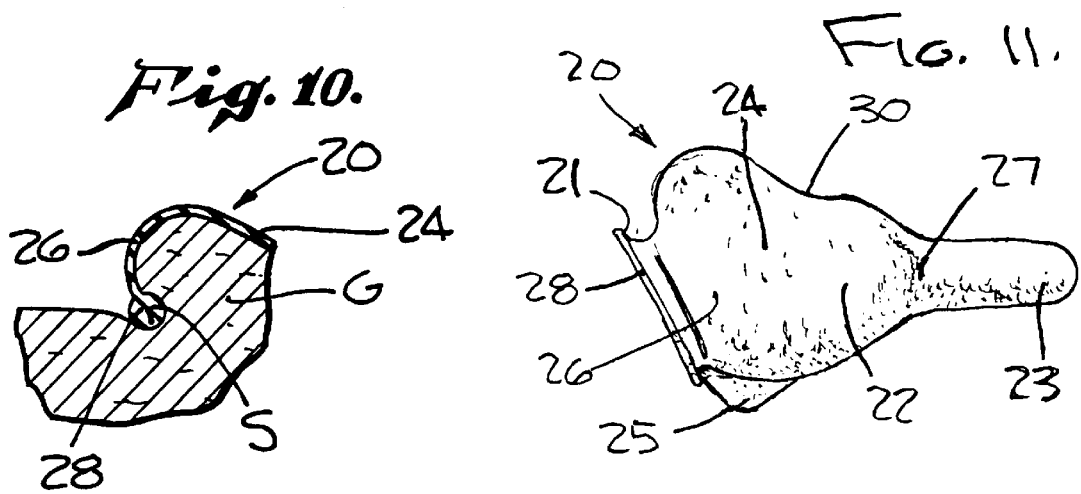

CONTOURED MICRO-CONDOM WITH RADIALLY STRETCHING APPLICATOR

This application is a continuation of Ser. No. 08/613,463 filed Mar. 11, 1996.

FIELD OF THE INVENTION

This invention relates to a miniature prophylactic contraceptive device, fitting over only the glans of the male sex organ, and to an associated combined applicator and package for ease of use and application.

BACKGROUND OF THE INVENTION

There are many variations in the art of prophylactic contraceptive devices and applicators. This invention is an abbreviated prophylactic device with a combined applicator and self-contained packaging for storage and transportation. The contoured micro-condom has been designed to alleviate some of the problems associated with the use of condoms, namely, decreased sensitivity during intercourse with full-sized condoms, and a tendency for rolling off the penis during usage, a problem with prior abbreviated condoms.

The instant applicator/package has been designed to alleviate prior problems with storing and opening condoms before use. It makes it easy to apply the micro-condom in the dark with only a few simple steps which should take only seconds to do.

The micro-condom with combined Unidirectionally releasing applicator/package is designed to be pre-assembled to eliminate some potential problems associated with condom application. Currently, there are no known micro-condoms which are designed with a separate applicator or a separate combined applicator and package. There are also no known combination applicators and packages designed for micro-condoms. The instant design eliminates the inherent clumsiness of application, a major problem in the related art.

The combined unidirectionally releasing applicator/package itself is distinguishable from other methods or devices in the field of contraceptive devices.

Typical rolled condoms, other rolled condoms with pull tabs, or accordion-style applicators, as have been priorly associated with conventional full condoms, can be problematic or impractical for abbreviated condoms such as in the instant invention. The combined unidirectionally releasing applicator/package in this invention is used to both package, protect, and easily apply the microcondom. This synergistic combination eliminates typical problems of condom use, such as having to tear tough packages, take a flaccid condom out of a loose package, unroll it to its proper length before applying, and unroll the remainder upon the penis.

The unidirectionally releasing applicator/package differs fundamentally from other known applicators in the art because of how it works and how it is constructed. The instant micro-condom is placed within a retainer frame, with its banded open end fitted within a constraining structure of the retainer frame, and is perfectly aligned for penetrating a unidirectionally resistive, or releasing upper cover.

A combination of deformable material and/or strategic structure of the upper cover makes the upper cover able to withstand nominal external forces (e.g. from transportation or storage) in one direction, yet able to expand or break from forces in the opposite direction to release the microcondom within. There are no known applicators with this feature as in the instant invention.

The shape of the instant micro-condom within the releasing applicator/package is also novel. Conventional, full-size condoms typically have a longer tubular sheath with a conical closed top and covers the entire shaft and head of the penis.

Prior abbreviated condoms typically are conical or even "frustro-conical" in shape. U.S. Pat. No. 4,820,290 discloses an abbreviated condom with a hood and wide band, the hood being in configuration similar to conventional condoms (conical) in order to receive fluid in the interstices.

U.S. Pat. No. 4,869,269 discloses a "frusto-conical" shaped micro-condom with receptacle. The instant condom is shaped to closely approximate the slopes of a glans penis head continuous through the glans sulcus, in general form. Additionally, it is not necessary to provide an indenture in the condom as described by this reference.

Prior abbreviated condoms also use different means for securing the sheath to the penis. U.S. Pat. No. 4,820,290, for example, discloses the use of an extra wide band coupled to a conical sheath.

U.S. Pat. No. 4,869,269 discloses the use of a medical grade adhesive to form a seal between the glans and the condom, wherein an inside layers must be peeled off first before application. In the instant invention, a narrow elastic band fits snugly within the coronal sulcus of the glans penis and prevents it from coming off during intercourse or when the penis is tumescent.

OBJECTS OF THE INVENTION

A main objective of the present invention is to provide a condom which provides less of a barrier during sexual intercourse while at the same time being safe and effective against diseases and pregnancy, and which is easy to use.

As a consequence of this objective, an advantage of this invention is greater comfort for the user and a greater likelihood that contraception will be used to avoid diseases and unwanted pregnancies.

It is yet another main objective to provide a quick, easy and carefree applicator and package for the above contraceptive device which greatly reduces the time and number of steps required to place the device upon the penis.

A further objective is to provide a contraceptive device having the above attributes which is very easy to remove.

SUMMARY OF THE INVENTION

The foregoing objectives and other advantages are attained by a contoured micro-condom suitable for pre-assembly with a combination unidirectionally releasing applicator and package.

One aspect of the invention, a tapering design, enhances the fit and comfort of a micro-condom and simultaneously better prevents problems of rolling and slippage during use.

The contoured micro-condom, alone or assembled within the instant applicator/package, consists of a specially contoured hood of impervious elastic material, shaped and sized approximately to conform to the glans penis shape and a narrow elastic band shaped and sized especially for placement into the coronal sulcus of the glans. The more exact nonlinear tapering of the radii to approximate the curves of a nominal glans penis enhances the fit over just a frusto-conical shaped micro-condom.

Another aspect of the invention, a more complex tapering design, further enhances the ability to prevent slippage of the micro-condom. In addition to the natural nonlinear tapering in the above described design, the hood may also be additionally slightly tapered in a strategic spot to further secure the fit. The strategic spot corresponds with the spot on the micro-condom, generally along the middle of its length, which corresponds with the portion of the glans penis wherein the slope changes from concave to convex, outwardly, along the direction from the tip to the sulcus.

Yet another aspect of the invention protects and helps to apply the contoured micro-condom or any micro-condom in a quick, reliable, and easy way.

The applicator/package, which should be assembled with the contoured micro-condom or any micro-condom, since the contoured micro-condom has a correct orientation for fitting, is designed to withstand normal wear and tear and to make it easy to open and apply the micro-condom. Application may be made easier by an orientation indicator on the package and by a removable lower cover allowing penetration of the micro-condom through the applicator/package.

The applicator/package is comprised of a retainer frame and upper and lower covers which cover opposite ends of an apperature within the retaining frame. The retainer frame apperature holds the condom in place and preferably a constraining structure on an outer surface of the retaining frame holds the open end of the micro condom. The micro-condom is concentrically placed and pressed within the apperature within the retaining frame. The apperature within the retainer frame is sized and shaped sufficiently for a human erect penis to enter as it is applied to the micro-condom within.

In accordance with another aspect of the invention, the cover covering the closed end of the micro-condom in the described orientation, or the unidirectionally releasing cover, resists a change of shape and size of a structured material from a force from one direction, while being able to change to a size and shape sufficient for the entry through the cover of an erect glans penis, from a force from the opposite direction. It is comprised of a material with structure which is either deformable, expansive or breakable upon application of a force from an inside force (defined herein) and resistive to expansion, deformation, or breakage from an outside force (defined herein).

The cover covering the open end of the micro-condom, and the apperature of the retainer frame, is any easily removed lower cover attached to the retainer ring. This cover allows access to the micro-condom for application.

The instant applicator/package is a hollow retaining frame sandwiched between a lower removable cover, attached to the frame, and an upper unidirectionally releasing cover, also attached to the frame. A reference to outer herein means the accepted meaning of that term, that it is not surrounded by any other structure of the invention and exposed to the external environment.

The upper releasing cover protects the closed end of the micro-condom. The lower removable cover protects the open end of the micro-condom as it sits within the frame.

The retainer frame has an apperature therein with an approximate axis of symmetry and distal and proximate ends defined relative to the micro-condom therein. The open end of the micro-condom lies in or close to the proximate end plane, and the closed end of the micro-condom lies in or is close to the distal end plane. The proximate and distal ends further define upper and lower outside surface of the frame. The outer surface of the frame which intersects or is continuous with the proximate end plane is the lower outer surface. The outer surface which intersects or is continuous with the distal end plane is the upper outer surface of the frame. The upper and lower outside surfaces of the frame or proximate and distal end planes, define "inside" and "outside", directions of forces as defined herein. A force directed generally from the lower to upper outer surface planes, or proximate to distal end planes is an "inside", force, as defined herein. A force directed from the upper to the lower outside surface planes, or distal to proximate end planes, is an "outside" force as defined herein.

A micro-condom, fitted for the glans penis head, is pressed along its axis of symmetry, so any layers lie concentrically, and is placed within the apperature. The micro-condom's closed end is thereby pressed and contained by the upper releasing cover, and its open end is thereby pressed and contained by lower cover.

In accordance with another aspect of the invention, the lower outer surface of the frame may preferably have a closed loop constraining structure (e.g. a groove) for a micro-condom band, which lies concentrically (or equivalently), around the proximate end of the apperature. The radially sliced cross-section (radial from the approximate axis of symmetry of the apperature) of the constraining structure is shaped (e.g. annular or other conic section) to allow slight grasping and holding of the corresponding micro-condom band which is placed therein. The micro-condom has a band at its open end which is preferably placed within the constraining structure of the frame. The constraining structure is preferably in the lower outer surface of the frame, allowing the open end of the micro-condom to be slightly widened and ready to receive the erect glans penis head. With the placement of the penis therein, the sufficient inside force may be supplied to either expand or break the upper releasing cover, and also to release the band from any constraining structure. In this way, compared to known condoms, only a few easy steps are required for unpackaging AND application—removal of lower cover, proper orientation, and placement within the micro-condom.

One embodiment for the unidirectionally releasing upper cover is a deformable crushed cover, having surface area, shape and volume (above the distal end plane), in its expanded state, sufficient to contain a nominal erect glans penis head. Another is an elastic dome-shaped cover having similar surface area, shape and volume properties.

A preferred deformable material would be Mylar. A preferred crushed geometry, which can be used with deformable material, is an irised geometry. One embodiment of the irised geometry has layers radiating from the circumference, periphery or edge (e.g. where upper and lower surfaces are bridged or intersected by another surface) of the frame, toward the midpoint of the upper cover, the layers and irising which may stop before reaching the midpoint. In this embodiment, Mylar is pressed from the outside of the dome-shaped material, or its concave side, which layers the Mylar outwardly, allowing it to readily expand outwardly with an "inside" force, but not inwardly with an "outside" force.

Another preferred material for the upper cover is foil, or a thin metallic material which is deformable.

Yet other preferred embodiments of the unidirectionally releasing cover, would be covers which are selectively weakened toward the upper cover's midpoint or relatively small area around its midpoint. For example, a flat or pressed dome-shaped cover may have tiny perforations or indentations or have weakened material in a radial spoke-like fashion emanating from the midpoint of the upper cover. Or the upper cover might be made of a gradually thinning material towards its midpoint. Or the upper cover, may have a small circular groove in the area of the midpoint.

The irised releasing cover cannot be easily punctured from the outside of the package because the layers are stacked up on top of each other toward the outside of the package and the inner side of the cover presses against the pressed micro-condom.

The selectively weakened releasing cover will be difficult to puncture because it must be pushed at the center to break the material easily. And the center of the cover also presses against the pressed condom on the inside of the cover. Also, weakening lying closer to the surface facing the inside of the frame enhances this feature. In this way, the upper releasing cover is both durable enough to the outside environment, yet easily broken from the inside upon penetrating the micro-condom from the opposite side within the retaining ring. This allows for the applicator to act dually as a package as well.

Several embodiments of the invention have been described herein. Furthermore, I have shown and described the preferred embodiments by way of illustration of the best mode contemplated by me for carrying out this invention. As the invention is capable of modification in various obvious aspects, and of different embodiments thereof, the drawings and descriptions are illustrative only, and not restrictive.

BRIEF DESCRIPTION OF THE FIGURES

A Preferred Embodiments Summary table is included which references each item in each figure.

FIG. 1 is the perspective view of the irised embodiment of the micro-condom in its pre-assembled applicator/package, showing the irised top cover attached to surfaces of the retainer ring.

FIG. 2 Is another perspective view of the irised embodiment of the micro-condom and applicator/package, shown from the lower cover, as it is peeled away to expose the concentric layering of the pressed micro-condom contained between the retaining ring's inner annular wall and the upper and lower covers.

FIG. 3 is a side view of the wall of the retainer ring exposing the cross sectional stratified layers of: top cover, retainer ring with groove, micro condom, and lower cover, it's lower groove containing the annular bead, and the micro-condom concentrically pressed within the retainer ring.

FIG. 4 is the same side view of the retainer ring as in FIG. 3, after removal of the lower peel-away cover for access to the micro-condom with annular bead.

FIG. 5 is a side view of the penis and micro-condom with the applicator/package as it is being applied to the penis, after the annular bead is released and the penis pushes through the micro-condom to expand the one-way releasing top cover.

FIG. 8 is a side view of the micro-condom completely applied to the penis.

FIG. 9 is a lower planar view of the micro-condom completely applied to the penis, as it would appear placed around the part of the penis containing an indentation, also called the frenulum.

FIG. 10 is a side cross sectional view of the micro-condom hood and annular bead as it would appear once positioned within the glans sulcus of the penis, after application of the micro-condom.

FIG. 11 is a perspective view of the micro-condom hood with annular bead, tabs and receptacle, as it would appear by itself.

DETAILED DESCRIPTION OF THE DRAWINGS

Figure 6:
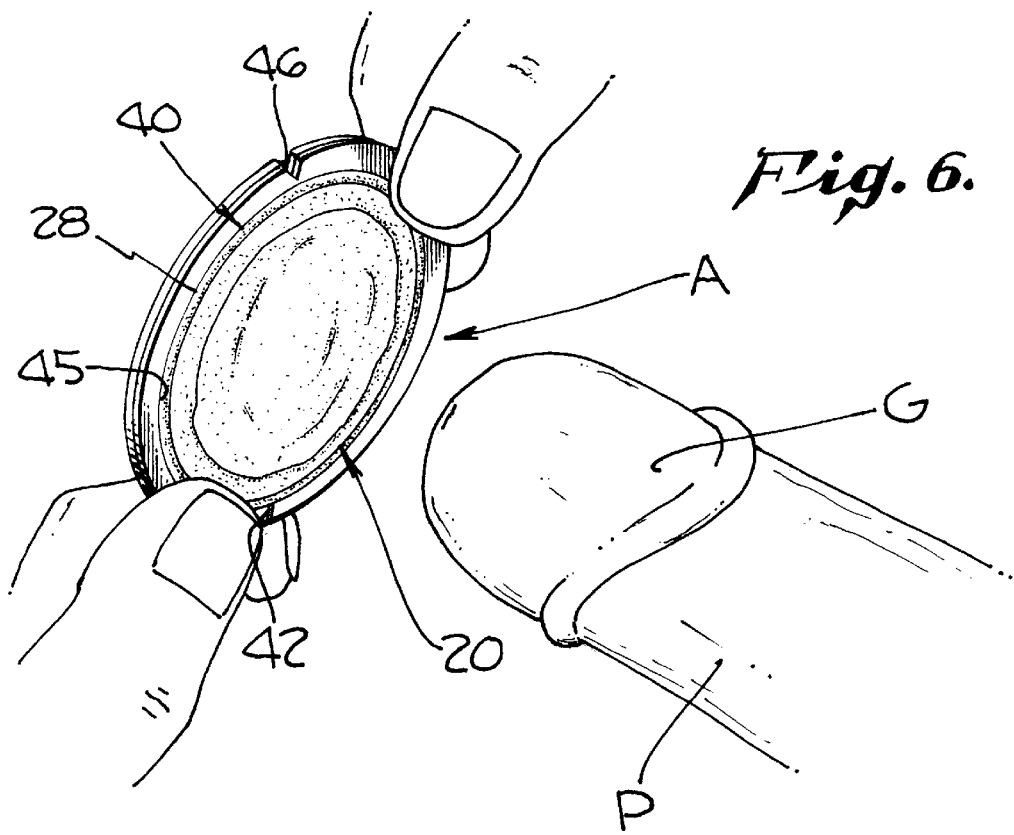
FIG. 6 is a perspective view of the bottom of the applicator/package, after the lower cover has been removed, with orienting notch and pressed micro-condom therein, as it would be oriented with respect to the penis, right before application to the penis.

The table may be referenced to indicate each item on each figure.

Referring to FIG. 11, the condom 20 has the shape of the glans penis head G when in its collapsed, unexpanded state, if it were not pressed within the retainer ring walls or applied to a penis.

With such shape, there may only be an approximate axis of symmetry depending on the embodiment, and the cross-sections perpendicular to any such axis of the micro-condom (it may vary along different sections) are only approximately circular. A reference to radii in this context means the radii of the approximate circular cross-section.

The contoured micro-condom 20 tapers according to the natural curves and contours of the glans penis head and sulcus S. Although shapes of this organ may vary, the micro-condom 20 is designed in accordance with a nominal shape having somewhat pronounced features or curvatures. Even these curvatures may be slight, however.

The closed end 27 of the micro condom as shown in FIG. 11 is the area where the tip of the micro-condom would be without a seminal receptacle 23. (Slopes and curvatures referenced herein mean slopes in the radius-length plane of a cylindrical coordinate system, length being along the approximate axis of symmetry.)

The midsection 22 is a general area spanning from the closed end 27 or seminal receptacle 23, which, in its expanded state, would fit over the part of the glans penis head which has a generally concave curvature from the outside continuing to the part of the penis having an inflection point, where the curvature or slope changes direction and the concave curvature becomes convex.

An end section 24 is similarly defined as the general area spanning from the inflection point described above at midsection 22, spanning the area of the micro-condom which would fit over the part of the glans penis head which has a generally slightly convex curvature to where the expanded micro-condom 20 would fit over the part of the glans which starts to curve inward toward the Sulcus S (generally the largest diameter of the glans penis P).

The periphery 26, similarly defines the general area of the micro-condom which spans from the end of the hood inflection 30 end section 24 (generally having the largest radius) which would fit over the part of the glans penis head having the largest radius, and continues to the open end 21 of the micro-condom, where it is in continuous connection with an annular bead 28.

In one simple embodiment, the micro-condom may have generally nonlinearly increasing radii from the closed end 27 of micro-condom without a seminal receptacle 23 or from the seminal receptacle 23 (if there is one) to the approximate area of end section 24, and generally nonlinearly decreasing radii from approximately end section 24 to periphery 26. Once placed upon the penis, the end section to periphery is fitted around the contours of the glans sulcus S behind the glans head G, as shown in FIGS. 8 and 10.

In another, more complex, embodiment it can contain receptacle 23 at its closed end 27, or not, and have generally nonlinearly increasing radii from either seminal receptacle 23 or closed end 27 to generally where end section 24 meets periphery 26, while also having radii tapering for a short section of the midsection 22 around where the micro-condom 20 would fit around the inflection point of the glans penis P, and changing a generally concave shape to a slightly convex shape along the end section 24, and again decreasing radii from end section 24 to periphery 26. The corresponding location of midsection 22, end section 24 and periphery 26, once upon the penis P is again shown in FIGS. 8 and 10.

This tapering effect caused by a variation in radii helps to further seal the condom and to maintain a tight fit while allowing enough space between the micro condom 20 and penis P. In the more complex embodiment, the addition of the small convex indentation around the midsection, further helps to secure the fit, and is an exaggeration of the natural contour of the penis head.

FIGS. 8 and 11 also shows a removal grip 25 on the micro-condom 10.

The optional, but preferred, seminal receptacle 23, shown in FIGS. 8, 9, 11, is of a sufficient size to contain normal amounts of seminal fluid from an ejaculation. It may preferably contain within it, small amounts of any known lubricant in the art, nonerosive to the material of micro-condom 20, for the purpose of closing the receptacle to avoid air traps within the receptacle 23.

FIGS. 8, 11, and 10 shows the placement of an annular bead or band 28 as it appears respectively, both on and off the penis. FIG. 10 shows how bead 28 fits snugly into the sulcus S. Bead or band 28 is any shaped band dimensioned to fit snugly within the sulcus S. It is relatively narrow, while being thicker than the material composing the remainder of the micro-condom 20.

FIG. 9 shows a lower planar view of how the grip 25 would be placed along the natural indention of the underside of the penis. The removal grip 25 can be any size or shape which allows the fingers to grip the material and pull the micro condom 20 off the penis by pulling the annular bead 28 out of the sulcus S. Placement of the grip 25 in the natural indentation of the penis P makes it easier to grasp and pull from the skin.

Referring next to FIG. 1, the applicator A encompasses three disk-shaped components assembled together: the retaining ring 40, the upper irised releasing cover 50, and the lower peel-away cover 32 of the applicator A. The retainer ring 40 acts as the supporting frame for all the elements of the applicator A.

In FIG. 1, the upper irised cover 50 is created by pressing a dome-shaped (or hemisphere) of Mylar or foil or any similarly functioning material, such that an irised portion 51 is created and a smooth portion 53 results generally in the middle of the cover as shown. Attached portion 52 is where the upper irised cover 50 is secured or glued onto the retainer ring 40. The desirable properties of the Mylar or foil are that those materials are deformable and can be reshaped, the material retaining memory of the new shape, being permanently deformable.

FIG. 2 shows the lower peel-away cover 32 as it is being removed from the lower surface of the retainer ring 40, and exposing the micro-condom 20 within as its annular bead 28 sits within the the retainer ring 40. The pull tab 33 on the lower cover 32 makes it easier to remove the lower cover 32. An orienting lower retaining notch 36 is shown in FIGS. 1–2 and is placed at any arbitrary point on the applicator A to orient the user to the correct placement of the micro condom 20.

FIGS. 3–4 show a cutaway views of the layers of the applicator A. The bead 28 sits within the annular groove 45 contained within retainer ring 40. In FIG. 3, retainer ring 40 is sandwiched between lower cover 32 and upper cover 50. The micro-condom 20 is concentrically pressed and retained within the annular inner retainer ring wall 48 in the radial direction and the upper cover 50, and lower cover 32 in the other directions. FIG. 4 shows the view without the lower cover 32.

FIG. 5 depicts how the upper irised cover 50 would unfurl, expand, enlarge and change shape, once the bead 28 is placed within the sulcus S and the micro-condom 20 is secured around the penis P as it pushes out the upper irised cover 50. It further shows the exposed lower surface 47 of the retainer ring 40, and covered upper surface 49.

Figure 7:
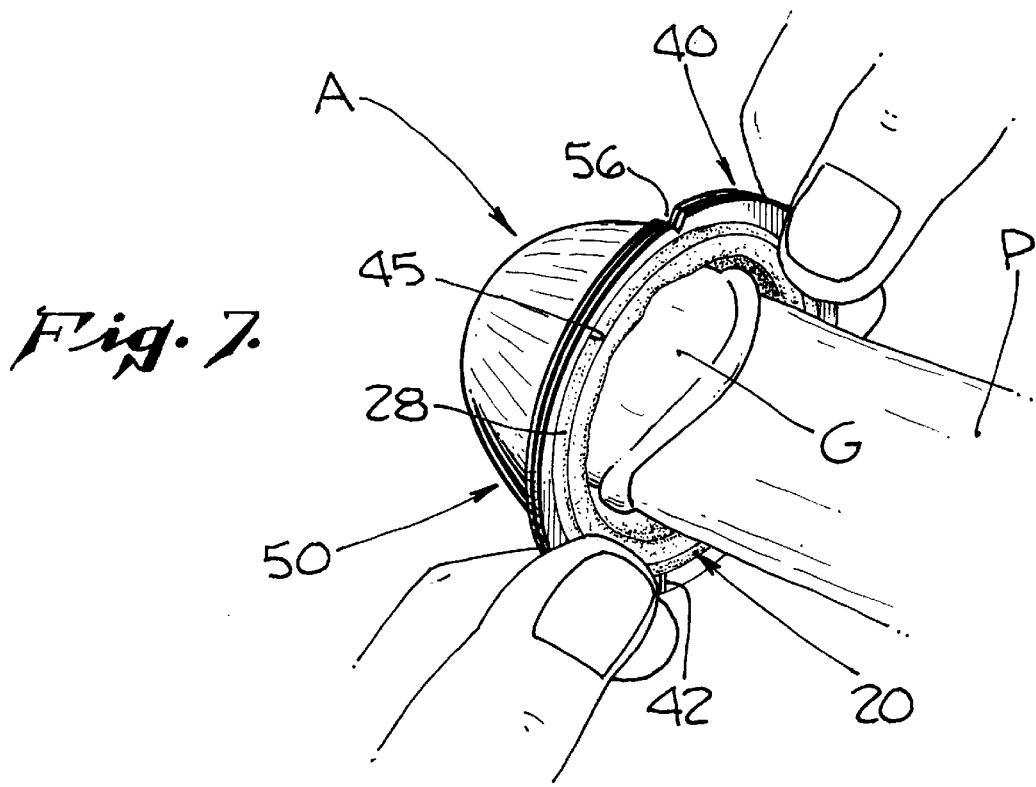
FIG. 7 is a perspective view of the applicator/package with micro-condom and orienting notch, as it is applied to the penis and as the top irised releasing cover expands to make room for the expanding micro-condom within.

FIG. 6 shows the orientation of the applicator A with micro-condom 20, after the lower cover 32 has been peeled away, as it would appear from the bottom, just before placement onto the penis P. The lower orienting notch 46 designates what direction the applicator should be placed before application. FIG. 7 shows how the upper irised top cover 50 would appear as it is being released or expanded by the entering penis P during application, and before the bead 28 is released from the annular groove 45.

Figure 12:
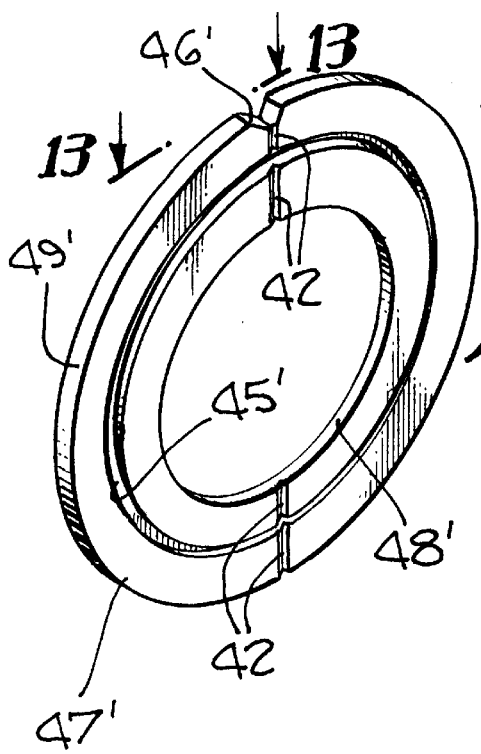
FIG. 12 is a perspective view of a breakable retainer ring with orienting notch.
Figure 13:
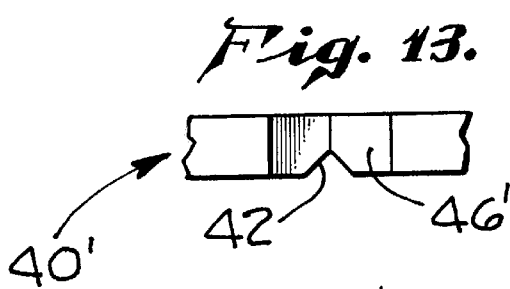
FIG. 13 is a cut-away side view of the weakened retainer ring cut through its orienting notch

FIG. 12 depicts a breakable retaining ring 40'. The ring has a weakening groove 42 cut from the orienting notch 46' to the point on the outer circumference of the breakable retaining ring 40' which is 180° from the orienting notch 46'. This allows for the possible breaking of the applicator after application, if desired. It may be used incase of a tighter than normal fit between the penis P and applicator A. Lower surface 47' and upper surface 49' are shown as well. The annular groove 45' is shown within lower surface 47'. This figure shows how a cylindrical apperature is formed by inner wall 48', proximate and distal planes lying between the open edges of the inner wall 48'. FIG. 13 shows the shape of the weakening groove 42 from the orienting notch 46'. Annular groove 45' is also shown on the lower surface of retainer ring 40'.

Figure 14:
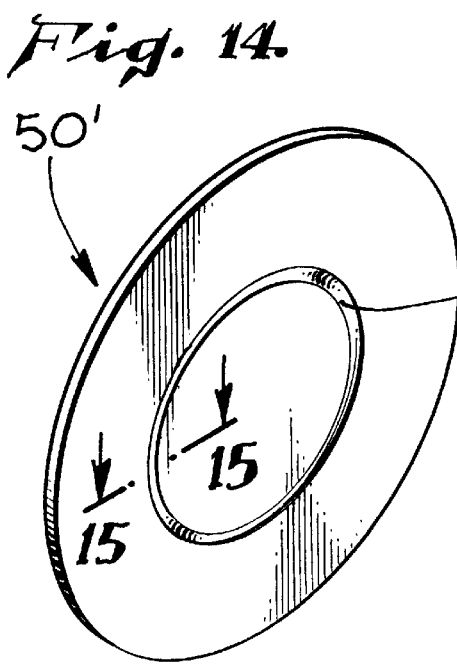
FIG. 14 is a perspective view of the circularly weakened releasing cover.
Figure 15:
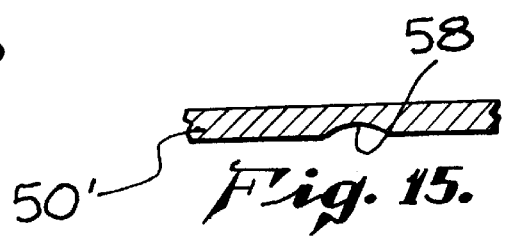
FIG. 15 is a side view of the annular grooves used to weaken the releasing cover of FIG. 14.

FIG. 14 depicts an alternate embodiment of the unidirectionally releasing upper cover 50 of FIG. 1. The upper cover 50' depicts a flat piece of Mylar, foil or similarly functioning material, having a weakening annular groove 58 of circular shape placed near the center of the upper cover 50'. The weakening annular groove 58 is shown in FIG. 15 as it would appear in a side cross sectional slice. The surface of cover 50' containing groove 58 faces the inside of the retainer ring 40, and lies adjacent to the micro-condom 20 lying withing the apperature formed by inner wall 48. This orientation weakens the cover 50' more on the inside than on the outside.

Figure 16:
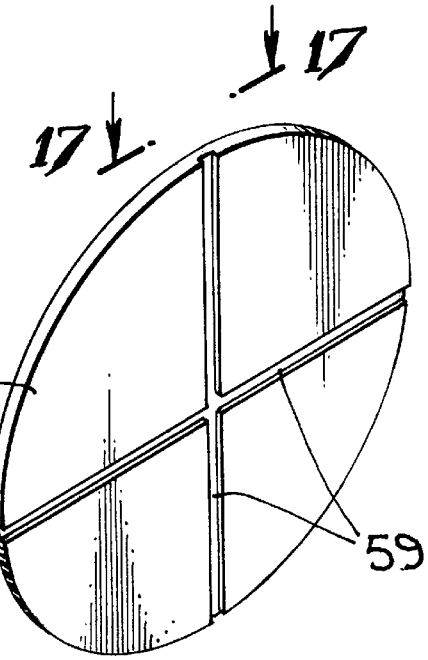
FIG. 16 is a perspective view of the spoke-like weakened releasing cover.
Figure 17:
FIG. 17 is the side view of the square grooves used in the releasing cover of FIG. 16.

FIG. 16 shows yet another embodiment for a weakened upper cover 50", which is flat. This time, the square grooves 59 are in a spoke-like fashion from the center of the upper cover 50", The weakest point of the upper cover 50" is at the midpoint thereof, making it easy for the penis P to penetrate the upper cover 50" as described. FIG. 17 further depicts a square weakening groove 59 as it appears in a side cross section. The surface of cover 50" containing square groove 59 faces the inside of the retainer ring 40, and lies adjacent to the micro-condom 20 lying withing the apperature formed by inner wall 48. This orientation weakens the cover 50" more on the inside of the retainer ring 40 than on the outside.

The upper covers 50' and 50" may also be created from a pressed dome-shaped piece of material as well. The preferred shape depends upon the material used, its strength, and thickness.

I claim:

1. An abbreviated micro-condom comprising,
   a hood of impervious elastic material in the shape of the glans penis head including glans sulcus, having an axis of symmetry, and varying radii along said axis, a closed end, an open end, a midsection, an end section, and a periphery, said hood tapered, such that, from said closed end to said open end, the radii generally increases in a nonlinear fashion along said midsection and said end section, and then generally decreases in a nonlinear fashion along said periphery, generally following the contours of the natural glans penis head, enhancing the fit of said hood upon the erect glans penis head, said hood having sufficient volume and elasticity to accommodate a nominal amount of seminal fluid, and
   a constrictive band sized and shaped according to a nominal coronal sulcus to fit snugly yet comfortably within the coronal sulcus, said band being in continuous sealed connection with said open end,
   wherein the size and shape of said micro-condom results in a snug, yet comfortable fit over the erect glans penis head and sulcus.

2. A combination applicator and packaging with micro-condom, comprising:
   1) a retainer frame having upper and lower surfaces, at least one inner wall and an aperture therethrough defined by said at least one inner wall which intersects said upper and lower surfaces, said aperture sufficiently sized to accommodate an erect glans penis head,
   2) a means for holding said micro-condom in place within said aperture and for holding said open end in a position to accept an erect glans penis head,
   3) a unidirectional releasing upper cover sealing said aperture, said releasing upper cover comprising, structured material selected from the group consisting of deformable structured material, expansive structured material, and breakable structured material, for enabling said upper cover to change shape from an inside force and to resist an outside force,
   4) a lower cover, sealing said aperture at said lower surface,
   5) a micro-condom sized to fit upon the glans penis head and sulcus, having an open end and a closed end, pressed within said aperture, said open end flush against said lower cover and said closed end flush against said unidirectional releasing upper cover,
   wherein said applicator and package with micro-condom effectively protects and stabilizes the micro-condom and enables easy application.

3. The invention of claim 2 wherein said micro-condom further comprises, a hood of impervious elastic material in the shape of the glans penis head including glans sulcus, having an axis of symmetry, and varying radii along said axis, a midsection, an end section, and a periphery, said hood tapered such that, from said closed end to said open end, the radii generally increases in a nonlinear fashion along said midsection and said end section, and then generally decreases in a nonlinear fashion along said periphery, generally following the contours of the natural glans penis head, enhancing the fit of said hood upon the erect glans penis head, and having sufficient volume and elasticity to accommodate a nominal amount of seminal fluid when placed upon a glans penis head and sulcus, and
   a constrictive band, being sized and shaped according to a nominal coronal sulcus to fit snugly yet comfortably within the coronal sulcus, in continuous sealed connection with said open end.

4. The invention of claim 3 wherein said unidirectional releasing upper cover is a deformable compressed dome which when upon said retainer frame, has a generally concave shape from outside said retainer frame in its uncompressed state.

5. The invention of claim 2 wherein said micro-condom further comprises,
   a hood of impervious elastic material in the shape of the glans penis head including glans sulcus, having an axis of symmetry, and varying radii along said axis, a closed end, an open end, a midsection, an end section and a periphery, said hood tapered such that, from said closed end to said open end, said radii generally increases in a nonlinear fashion along said midsection to render a generally concave shape along said midsection into a convex shape along said end section, said radii generally increases in a nonlinear fashion along said end section to render a convex shape along said end section, and generally decreases along said periphery, generally following the contours of the natural glans penis head, enhancing the fit of said hood upon an erect glans penis head, and having sufficient volume and elasticity to accommodate a nominal amount of seminal fluid, and
   a constrictive band, sized and shaped according to a nominal coronal sulcus to fit snugly yet comfortably within the sulcus in continuous sealed connection with said open end.

6. The invention of claim 5 further comprising at least one removal grip close to said band the corresponding area to be placed around the natural indentation of the underside of the glans penis head, sufficient for holding between two fingers, wherein removal of the micro-condom is facilitated.

7. The invention of claim 5 wherein said unidirectional releasing upper cover is a deformable compressed dome which when placed upon said retainer frame, has a generally concave shape from outside said retainer frame in its uncompressed state.

8. The invention of claim 2 further comprising a means for identifying a correct orientation of said retainer frame for application, and
   wherein the means for holding said micro-condom is a groove within said lower surface matching said constrictive band and lightly holding said band around said aperture.

9. The invention of claim 8 further comprising a means for breaking said retainer frame in at least two parts, wherein removal of said frame from the penis is easier.

10. The invention of claim 9 wherein said means for breaking is a line of weakness within said lower surface, emanating from said identifying means and bisecting said lower surface such that when said retainer frame is broken therefrom, said aperture is split into substantially equal volumes.

11. The invention of claim 2 wherein said unidirectional releasing upper cover is a deformable compressed dome which when upon said retainer frame, has a generally concave shape from outside said retainer frame in its uncompressed state.

12. The invention of claim 11 wherein said unidirectional releasing cover is made of Mylar.

13. The invention of claim 11 wherein said unidirectional releasing cover is made of a thin metallic sheet.

14. The invention of claim 11 wherein said deformable compressed dome is compressed in an irised fashion.

15. The invention of claim 2 wherein said unidirectional releasing cover is of elastic material.

16. The invention of claim 2 wherein said unidirectional releasing upper cover has a midpoint and is a sheet of material weakened around said midpoint.

17. The invention of claim 16 wherein said unidirectional upper releasing cover further comprises at least two lines of weakness intersecting each other at said midpoint.

18. The invention of claim 16 wherein said unidirectional releasing upper cover further comprises a small circle of weakness around said midpoint.

19. An abbreviated micro-condom comprising,
- a hood of impervious elastic material in the shape of the glans penis head including glans sulcus, having an axis of symmetry, and varying radii along said axis, a closed end, an open end, a midsection, an end section and a periphery, said hood being tapered such that, from said closed end to said open end, said radii generally increases in a nonlinear fashion along said midsection so as to render a generally concave shape along said midsection into a convex shape along said end section, said radii generally increasing in a nonlinear fashion along said end section so as to render a convex shape along said end section, and generally decreasing along said periphery, generally following the contours of the natural glans penis head, enhancing the fit of said hood when placed upon an erect glans penis head, said hood having sufficient volume and elasticity to accommodate a nominal amount of seminal fluid when placed upon a glans penis head and sulcus, and
- a constrictive band sized and shaped according to a nominal coronal sulcus to fit snugly yet comfortably within the sulcus, said band being in continuous sealed connection with said open end,
- wherein the size and shape of the micro-condom results in a snug, yet comfortable fit over an erect glans penis head and sulcus.

20. The invention of claim 19 further comprising,
- a seminal receptacle of sufficient volume to accommodate a nominal amount of seminal fluid, in continuous connection with said closed end, and
- a sufficient amount of lubricant, placed within said seminal receptacle, for eliminating any trapped air therein, by collapsing said receptacle.

* * * * *